(12) United States Patent
Magil et al.

(10) Patent No.: US 7,037,504 B2
(45) Date of Patent: May 2, 2006

(54) EPIDERMAL GROWTH FACTOR PROTEIN AND GENE, AND METHODS OF USE THEREFOR

(75) Inventors: Sheila G. Magil, Arlington, MA (US); Susan D. Jones, Lexington, MA (US); Gary W. Pace, Winchester, MA (US); Stephen J. Brand, Lincoln, MA (US)

(73) Assignee: Waratah Pharmaceuticals, Inc., Verdun (CA)

( * ) Notice: Subject to any disclaimer, the term of this patent is extended or adjusted under 35 U.S.C. 154(b) by 463 days.

(21) Appl. No.: 10/000,840

(22) Filed: Oct. 23, 2001

(65) Prior Publication Data

US 2003/0171269 A1 Sep. 11, 2003

(51) Int. Cl.
| | |
|---|---|
| A61K 38/18 | (2006.01) |
| C07K 14/485 | (2006.01) |
| C12N 15/00 | (2006.01) |

(52) U.S. Cl. .................... 424/198.1; 530/324; 435/69.1
(58) Field of Classification Search .............. 424/198.1; 530/324, 399; 435/69.1; 514/2
See application file for complete search history.

(56) References Cited

U.S. PATENT DOCUMENTS

| | | | |
|---|---|---|---|
| 3,917,824 A | 11/1975 | Camble et al. | ............. 424/177 |
| 4,686,283 A | 8/1987 | Nestor, Jr. et al. | .......... 530/327 |
| 4,760,023 A | 7/1988 | Miyoshi et al. | ........ 435/252.33 |
| 5,102,789 A | 4/1992 | Siegel et al. | ............... 435/69.4 |
| 5,434,135 A | 7/1995 | Parikh et al. | .................. 514/12 |
| 5,705,485 A * | 1/1998 | Cini et al. | ..................... 514/12 |
| 5,885,956 A | 3/1999 | Nardi et al. | .................... 514/2 |
| 6,242,666 B1 | 6/2001 | Sarvetnick et al. | ............ 800/18 |
| 6,271,436 B1 | 8/2001 | Piedrahita et al. | ............. 800/21 |
| 6,288,301 B1 | 9/2001 | Nardi et al. | ................... 800/18 |

FOREIGN PATENT DOCUMENTS

| | | |
|---|---|---|
| WO | WO 93/03757 | 3/1993 |
| WO | WO 00/29438 | 5/2000 |

OTHER PUBLICATIONS

Simpson et al., "Rat epidermal growth factor: complete amino acid sequence", Eur. J. Biochem., 153:629–637 (1985).*
Database GenCore on EST, ID I52995, SAGGI, S.J., et al., "Epidermal Growth Factor Precursor–Rat", Gene Sequence, Jun. 1999.
Database GenCore on EST, ID AAP61038, Fujisawa Pharm KK, "Urogastron Precursor for Chemical Synthesis", Gene Sequence, Jul. 1991.
International Search Report for International Application No. PCT/US02/33907, mailed Jul. 29, 2003.
"The Isolation of the Urogstrones—Inhibitors of Gastric Acid Secretion—from Human Urine", Hoppe–Seyler's Z. Physiol. Chem., Bd.356, pp. 1765–1774, Nov. 1975.
Carpenter et al., "Human Epidermal Growth Factor and the Proliferation of Human Fibroblasts", J. Cell. Physiol., vol. 88, pp. 227–238, 1976.
Hollenberg et al., "Epidermal Growth Factor–Urogastone: Biological Activity and Receptor Binding of Derivatives", Molecular Pharmacology, vol. 17, pp. 314–320, Jan. 10, 1980.
Koch et al., "Molecular Species of Epidermal Growth Factor Carrying Immunosuppressive Activity", Journal of Cellular Biochemistry, vol. 25, pp. 45–59, 1984.
DiAugustine et al., "Evidence for Isoaspartyl (Deamidated) Forms of Mouse Epidemal Growth Factor", Analytical Biochemistry, vol. 165, pp. 420–429, 1987.
George–Nascimento et al., "Characterization of Recombinant Human Epidermal Growth Factor Produced in Yeast", Biochemistry, vol. 27, pp. 797–802, 1988.
Gregory et al., "The Contribution of the C–terminal Undecapeptide Sequence of Urogastone–Epidermal Growth Fator to its Biological Action", Regulatory Peptides, vol. 22, pp. 217–226, 1988.
Burgess et al., "Murine Epidermal Growth Factor: Structure and Function", Biochemistry, vol. 27, pp. 4977–4985, 1988.
Araki et al., "Stability of Recombinant Epidermal Growth Factor in Various Solutions", Chem. Pharm. Bull., vol. 37, No. 2, pp. 404–406, 1989.
George–Nascimento et al., "Replacement of a Labile Aspartyl Residue Increases the Stability of Human Epidermal Growth Factor", Biochemistry, vol. 29, pp. 9584–9591, 1990.
Clare et al., "Production of Mouse Growth Factor in Yeast: High–Level Secretion Using *Pichia pastoris* Strains Containing Multiple Gene Copies", vol. 105, pp. 205–212, Jun. 18, 1991.
Kuo et al., "Pharmacokinetic Evaluation of Two Human Epidermal Growth Factors (hEGF51 and hEGF53) in Rats", Drug Metabolism and Description, vol. 20, No. 1, pp. 23–30, Oct. 7, 1991.
Karnes, Jr., William E., "Epidermal Growth Factor and Transforming Growth Factor–α", Galanin: Biochemistry and Physiology, pp. 553–586, 1994.
Shin et al., "Synthesis and Biological Activity of N–Terminal–Truncated Derivatives of Human Epidermal Growth Factor (h–EGF)", Peptides, vol. 16, No. 2, pp. 205–210, 1995.

(Continued)

*Primary Examiner*—James Ketter
*Assistant Examiner*—Nancy Vogel
(74) *Attorney, Agent, or Firm*—Ivor R. Elrifi, Esq.; David E. Johnson, Esq.; Mintz, Levin, Cohn, Ferris, Glovsky and Popeo, P.C.

(57) ABSTRACT

Forms of epidermal growth factor that are resistant to proteolysis, and gene sequences encoding these forms and having codons optimized for usage by an industrial production organism, are provided.

49 Claims, 6 Drawing Sheets

OTHER PUBLICATIONS

Playford et al., "Epidermal Growth Factor is Digested to Smaller, Less Active Forms in Acidic Gastric Juice", Gastroenterology, vol. 108, pp. 92–101, 1995.

Sizemore et al., "Impact of Receptor Downregualtion on Clearance of Two Human EGFs With Different Receptor Binding Activity", Peptides, vol. 17, NO. 7, pp. 1229–1236, 1996.

Goodlad et al., "Comparison of the Mitogenic Activity of Human Epidermal Growth Factor I–53 and Epidermal Growth Factor I–48 in vitro and in vivo", vol. 91, pp. 503–507, Jun. 25, 1996.

Gasslander et al., "Trophic Effects by Epidermal Growth Factor on Duodenal Mucosa and Exocrine Pancreas in Rats", Eur Surg Res, vol. 29, pp. 142–149, 1997.

Calnan et al. Potency and Stabiliy of C Terminal Truncated Human Epidermal Grwoth Factor, Gat, vol. 47, pp. 622–627, Jun. 1, 2000.

* cited by examiner

AAC TCT GAC TCC GAA TGT CCA TTG TCT CAC
asn ser asp ser glu cys pro leu ser his

GAC GGT TAC TGT TTG CAC GAC GGT GTT TGT
asp gly tyr cys leu his asp gly val cys

ATG TAC ATC GAA GCT TTG GAC AAG TAC GCT
met tyr ile glu ala leu asp lys tyr ala

TGT AAC TGT GTT GTC GGT TAC ATC GGT GAA
cys asn cys val val gly tyr ile gly glu

AGA TGT CAA TAC AGA GAC TTG AAG TGG TGG
arg cys gln tyr arg asp leu lys trp trp (G)        AA T TG A GA T AA
deletion   asn   stop

PANEL A
FIG. 1A

```
AAC TCT GAC TCC GAA TGT CCA TTG TCT CAC
asn ser asp ser glu cys pro leu ser his GAC GGT TAC TGT TTG CAC GAC GGT GTT TGT
asp gly tyr cys leu his asp gly val cys ATG TAC ATC GAA GCT TTG GAC AAG TAC GCT
met tyr ile glu ala leu asp lys tyr ala TGT AAC TGT GTT GTC GGT TAC ATC GGT GAA
cys asn cys val val gly tyr ile gly glu AGA TGT CAA TAC AGA GAC TTG AAG TGG TGG
arg cys gln tyr arg asp leu lys trp trp GCT TGA GAT AA
ala stop
```

PANEL B

FIG. 1B

AAC TCT GAC TCC GAA TGT CCA TTG TCT CAC
asn  ser  asp  ser  glu  cys  pro  leu  ser  his GAC GGT TAC TGT TTG CAC GAC GGT GTT TGT
asp  gly  tyr  cys  leu  his  asp  gly  val  cys ATG TAC ATC GAA GCT TTG GAC AAG TAC GCT
met  tyr  ile  glu  ala  leu  asp  lys  tyr  ala TGT AAC TGT GTT GTC GGT TAC ATC GGT GAA
cys  asn  cys  val  val  gly  tyr  ile  gly  glu AGA TGT CAA TAC AGA GAC TTG AAG TGG TGG
arg  cys  gln  tyr  arg  asp  leu  lys  trp  trp CAA TGA GAT AA
gln  stop

PANEL C
FIG. 1C

```
AAC TCT GAC TCC GAA TGT CCA TTG TCT CAC
asn ser asp ser glu cys pro leu ser his GAC GGT TAC TGT TTG CAC GAC GGT GTT TGT
asp gly tyr cys leu his asp gly val cys ATG TAC ATC GAA GCT TTG GAC AAG TAC GCT
met tyr ile glu ala leu asp lys tyr ala TGT AAC TGT GTT GTC GGT TAC ATC GGT GAA
cys asn cys val val gly tyr ile gly glu AGA TGT CAA TAC AGA GAC TTG AAG TGG TGG
arg cys gln tyr arg asp leu lys trp trp TCT TGA GAT AA
ser stop
```

PANEL D

FIG. 1D

SEQUENCE LISTING

<160> NUMBER OF SEQ ID NOS: 6

<210> SEQ ID NO 1
<211> LENGTH: 53
<212> TYPE: PRT
<213> ORGANISM: Human EGF (epidermal growth factor)

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 51
<212> TYPE: PRT
<213> ORGANISM: Recombinant human EGF51N

<400> SEQUENCE: 2

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Ser Leu Lys
        35                  40                  45

Tyr Tyr Asn
    50

<210> SEQ ID NO 3
<211> LENGTH: 51
<212> TYPE: PRT
<213> ORGANISM: Recombinant human EGF51A

<400> SEQUENCE: 3

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Ala
    50

<210> SEQ ID NO 4
<211> LENGTH: 51
<212> TYPE: PRT
<213> ORGANISM: Recombinant human EGF51Q

<400> SEQUENCE: 4

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys

```
                        35                  40                  45

Trp Trp Gln
    50

<210> SEQ ID NO 5
<211> LENGTH: 51
<212> TYPE: PRT
<213> ORGANISM: Recombinant human EGF51S

<400> SEQUENCE: 5

Asn Ser Asp Ser Glu Cys Pro Leu Ser His Asp Gly Tyr Cys Leu His
  1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Ser
    50

<210> SEQ ID NO 6
<211> LENGTH: 161
<212> TYPE: DNA
<213> ORGANISM: Artificial Sequence
<220> FEATURE:
<223> OTHER INFORMATION: DNA encoding EGF51N

<400> SEQUENCE: 6
aactctgact ccgaatgtcc attgtctcac gacggttact gtttgcacga cggtgtttgt       60
atgtacatcg aagctttgga caagtacgct tgtaactgtg ttgtcggtta catcggtgaa      120
agatgtcaat acagagactt gaagtggtgg aattgagata a                          161
```

EPIDERMAL GROWTH FACTOR PROTEIN AND GENE, AND METHODS OF USE THEREFOR

FIELD OF THE INVENTION

The present invention relates to epidermal growth factor (EGF) protein sequences having increased resistance to proteolysis and equivalent potency to normal human EGF, and to gene sequences having optimal codon usage in industrial production organisms.

BACKGROUND

Full length, wild-type human epidermal growth factor (EGF; see SEQ ID NO: 1) is a 53 amino acid protein with a molecular weight of 6217 daltons and a variety of biological functions (Karnes, W., Epidermal growth factor and transforming growth factor alpha, 1994, Raven Press, New York). Modifications of the amino acid sequence at the C-terminus have been reporting both from construction of altered forms by recombinant DNA engineering genetic studies, and as observed with EGF isolated from nature. EGF is susceptible to both endo and exo proteases, and proteolytic attack occurs in the stomach on EGF produced in the salivary gland and swallowed, has been observed as well as with EGF in the blood stream (Araki et al., *Chem. Pharm. Bull.* 37(2), 404–406, 1989; Playford et al., *Gastronenterology*, 108, 92–101, 1996).

EGF that is equal to or less than 46 amino acids in length has lost substantial biological activities, in comparison to EGF species of chain lengths equal to or greater than 47 amino acids. There are contradictory data on the exact effect on chain length on functional biological activities such as affinity for receptors and in vivo rates of EGF clearance. EGF of lengths 47, 48 and 51 amino acids (indicated "EGF47", "EGF48", etc.) can inhibit stomach acid secretion (U.S. Pat. No. 3,917,824). Human EGF47 inhibits acid secretion with the same potency as EGF53, however retains only about one tenth of the potency to stimulate fibroblast growth (mitogenic activity; Hollenberg et al., *Molecular Pharmacology* 17, 314–320, 1980; Gregory et al., *Regulatory Peptides* 22, 217–226, 1988). As these foregoing references show, the fact that a composition demonstrates high biological activity with respect to one biological activity does not imply that all biological activities are present in amounts equipotent to the full length composition.

EGF52 is equipotent to EGF53, in terms of both inhibition of acid secretion and stimulation of cell proliferation. The mitogenic activity of mouse EGF is largely lost if the chain length is less than 48 amino acids (Burgess et al., Biochemistry 27, 4977–4985, 1988). Further, hEGF51 and EGF53 display similar pharmacokinetics (Kuo et al., *Drug Metabolism and Disposition* 20, 23–30, 1992). EGF51 has similar activities as EGF53 (Calnan et al., *Gut* 47, 622–627, 2000), except for the retention of immunosuppressive activity (Koch et al., *J. Molecular Biochemistry* 25, 45–59, 1984). EGF48 is reported to be stable to proteolysis and to retain biological activities (U.S. Pat. No. 5,434,135; Kuo et al. op.cit; Sizemore et al. *Peptides* 17, 1229–1236, 1996). However, EGF48 has significantly lower activity than EGF 53 (Goodlad et al., *Clinical Science*, 91, 503–507, 1996).

Correct formation of disulfide bonds and its biological activity are not affected by shortening of the N-terminus by up to 5 amino acids (Shin, S. et al., *Peptides* 16, 205–210, 1995; DiAugustine et al., Analytical Biochemistry 165, 420–429, 1987). Oxidation of the methionine residue at position 21 does not affect the biological activity of recombinant h-EGF produced by yeast (George-Nascimento et al. *Biochemistry*, 27, 797–802).

Recombinant EGF is degraded by microbial proteases during production. Recombinant hEGF53 produced in *Saccharomyces cerevisiae* is degraded to a sequence of 52 and then to 51 amino acids in length, as a result of protease activity during fermentation (George-Nascimento, *Biochemistry*, 27, 797–802, 1988). EGF produced by *Pichia pastoris* is degraded to a form having 48 amino acids that is stable, and which is described as retaining high biological activity. (U.S. Pat. No. 5,102,789). Similarly, mouse EGF produced and secreted by *Pichia pastoris* is partly degraded during fermentation to 51 amino acids in length (Clare et al., *Gene* 105, 205–212, 1991).

Comparison of these data raises questions regarding susceptibilities to proteolysis of various forms of EGF, and correlations between the lengths of these different forms and the extent of several different biological activities. Because biological activities are mediated by a family of receptors that can be differently expressed, i.e., are tissue specific, any relevant biological activity of a modified EGF must be tested for that activity, to ascertain its level of function, since a biological activity level is not necessarily predictable from data obtained using an assay of another biological activity.

EGF and EGF receptor ligands such as TGFα have been shown to comprise a treatment for diabetes (Nardi et al., U.S. Pat. No. 5,885,956, issued Mar. 23, 1999; and Nardi et al., U.S. Pat. No. 6,288,301, issued Sep. 11, 2001), a disease that has achieved epidemic proportions in the United States and elsewhere.

There is a need for EGF proteins that are stable to proteolysis, that are produced as a single molecular species in high yields in a safe and convenient production organism with reproducible composition and purity required for approval as a drug, and that retain substantial biological activity for such a therapeutic purpose.

SUMMARY OF THE INVENTION

In one embodiment, the present invention provides a composition comprising an amino acid sequence of length X, X being an integer that is at least 48 and not more than 53, such sequence (i) being substantively homologous to a portion of SEQ ID NO: 1 from position 1 to position X-1 of SEQ ID NO: 1, and (ii) having at position X an amino acid residue different from that found in SEQ ID NO: 1. In accordance with a related embodiment, the amino acid residue at position X is a neutral amino acid. The amino acid residue at position X is, for example, asparagine. Further, X is position 51. The composition has increased resistance to proteolysis in comparison with that of SEQ ID NO: 1. The biological activity is at least 75% of that of SEQ ID NO: 1, for example, the biological activity is at least 90% of that of SEQ ID NO: 1. The biological activity is selected from the group consisting of: mitogenesis, cytoprotection, inhibition of acid secretion, growth of a tissue precursor cell, differentiation of a tissue precursor cell, and growth and differentiation of a tissue precursor cell. Mitogenesis is determined by the effect of the amino acid sequence on rate of mitosis of epithelial cells. Acid secretion is determined in a gastric fistulated animal. Differentiation is determined by islet neogenesis or mucosal cell formation.

In accordance with related embodiments, X is a hydrophobic amino acid or X is a neutral amino acid, or X is a charged amino acid. In a related embodiment when X is a neutral amino acid, X can selected from glutamine, alanine, and serine.

In another embodiment, the invention provides a composition comprising an amino acid sequence substantially homologous to SEQ ID NO: 1, wherein the amino acid residue at position 51 of SEQ ID NO: 1 is an amino acid other than glutamic acid. The biological activity of the composition is at least 50% of that of SEQ ID NO: 1. For example, the biological activity of the composition is at least 75% of that of SEQ ID NO: 1, for example, the biological activity of the composition is at least 90% of that of SEQ ID NO: 1. The composition has a biological activity substantially equivalent to that of SEQ ID NO: 1. In accordance with a related embodiment, the amino acid residues at positions 1–50 are at least 75% identical to that of SEQ ID NO: 1.

In another embodiment, the invention provides a composition comprising an amino acid sequence selected from the group consisting of SEQ ID NOs: 2, 3 and 4. For example, the invention in one embodiment provides a composition as shown in SEQ ID NO: 2. Further, the invention in another embodiment provides a polypeptide of 51 amino acids in length, wherein residues 1–50 are substantially homologous to the amino acid sequence as shown in SEQ ID NO: 1, and residue 51 is an asparagine residue. The polypeptide has increased resistance to proteolysis in comparison with that of SEQ ID NO: 1.

In a related embodiment, the invention provides a polypeptide wherein at least one of residues 1–50 is a conservative substitution of an amino acid in the sequence as shown in SEQ ID NO: 1. The polypeptide in a related embodiment further comprises a deletion of at least one of residues selected from positions 1–5 as shown in SEQ ID NO: 1. The polypeptide has at least 50% of a biological activity of human EGF as shown in SEQ ID NO: 1.

In another embodiment, the invention provides a composition comprising a human epidermal growth factor (EGF) having an amino acid sequence substantially homologous to that of at least positions 1–47 as shown in SEQ ID NO: 1, and having at least one amino acid replacement at positions 48–53 of the EGF carboxy terminus, the amino acid sequence being more stable to proteolysis than that of SEQ ID NO: 1. In a related embodiment, the amino acid sequence for residues at positions 1–50 is substantially as shown in SEQ ID NO: 1, and the residue at position 51 is an amino acid other than glutamic acid. The residue in a related embodiment at position 51 is selected from the group consisting of asparagine, glutamine, alanine, and serine, for example, the residue at position 51 is asparagine. At least 75% of the amino acids at positions 1–50 are as shown in SEQ ID NO: 1. The biological activity of the composition is at least 50% of that shown in SEQ ID NO: 1. The biological activity is selected from the group consisting of mitogenesis, cytoprotection, inhibition of acid secretion, growth of a tissue precursor cell, differentiation of a precursor cell, and growth and differentiation of a precursor cell. Mitogenesis is determined by rate of mitosis of epithelial cells. Acid secretion is determined in a gastric fistulated animal. Differentiation is determined by islet neogenesis or mucosal cell formation.

In another embodiment, the invention provides a pharmaceutical composition comprising an effective dose of a composition herein, in a pharmaceutically acceptable excipient. The pharmaceutical composition in a related embodiment, further comprises an additional therapeutic agent. For example, the additional therapeutic agent is a growth factor receptor ligand. For example, the ligand is a growth factor. For example, the ligand is a gastrin/cholecystokinin receptor ligand.

In a related embodiment, the invention provides a nucleotide sequence encoding an EGF composition herein, the nucleotide sequence having codons adjusted for optimum usage in an industrially acceptable production organism. The industrially acceptable production organism is a yeast. For example, the yeast is *Pichia pastoris*.

In a related embodiment, the invention provides a polynucleotide having a nucleotide sequence encoding a polypeptide of 51 residues in length and having a biological activity of human EGF, the sequence containing codons that are optimized for expression in a species of *Pichia*, and having an amino acid at the carboxyl terminus capable of conferring resistance to proteolysis. In related embodiments, the invention provides a recombinant strain of *Pichia* carrying a nucleotide sequence as shown in SEQ ID NO: 6; a recombinant strain of *Pichia* capable of producing the amino acid sequence as shown in SEQ ID NO: 2; and a nucleotide sequence encoding an amino acid sequence as shown in SEQ ID NO: 2.

In another embodiment, the invention provides a method of obtaining a composition comprising an amino acid sequence of length X, X being an integer that is at least 48 and not more than 53, such sequence (i) being substantively homologous to the portion of SEQ ID NO: 1 from position 1 to position X-1 of SEQ ID NO: 1, and (ii) having at position X an amino acid residue different from that found in SEQ ID NO: 1, the method comprising: designing a gene encoding the composition, having codons selected for optimum usage in an industrially acceptable organism; and producing the composition in the organism by fermentation of the organism.

In another embodiment, the invention provides a method of providing to a subject in need of regeneration of a tissue, a therapeutic composition comprising an amino acid sequence of length X, X being an integer that is at least 48 and not more than 53, such sequence (i) being substantively homologous to the portion of SEQ ID NO: 1 from position 1 to position X-1 of SEQ ID NO: 1, and (ii) having at position X an amino acid residue different from that found in SEQ ID NO: 1, the method comprising: obtaining the composition by the method according to claim 47; and administering to the subject the composition in an amount sufficient to effect regeneration of precursor cells, as a treatment of the subject for regeneration of the tissue. Accordingly, administering the composition is further administering an additional therapeutic agent. For example, the additional therapeutic agent is a growth factor receptor ligand. For example, the ligand is a growth factor. For example, the ligand is a gastrin/cholecystokinin receptor ligand. In related embodiments, X is the integer 51. The amino acid residue at X is a neutral amino acid. For example, the amino acid residue is asparagine. The composition is more resistant to proteolysis than the composition having a sequence as shown in SEQ ID NO: 1. In related embodiments, the subject is in need of islet cell regeneration, for example, subject has diabetes; or the subject is in need of mucosal cell regeneration.

In another embodiment, the invention provides a method of obtaining a modified amino acid sequence of an EGF that is more resistant to proteolysis than a nature identical EGF and that substantially retains a biological activity, the method comprising: identifying at least one residue of a sequence of the nature identical EGF that is subject to proteolysis by an industrially useful organism; designing the modified amino acid sequence in which the residue identified as subject to proteolysis is deleted or substituted with a different amino acid; and providing the modified amino acid sequence and testing proteolysis in comparison to the nature identical EGF, to obtain a modified EGF that is more resistant to proteolysis than the nature identical EGF. Accordingly, the nature identical EGF is from a human. Designing the modified amino acid sequence is, in a related embodiment, substituting at least one amino acid for at least one carboxy terminal residue, to obtain a new carboxy terminal amino acid sequence, such that the modified EGF is more resistant to proteolysis. In a related embodiment, identifying the at least one residue that is subject to proteolysis is determining a site of proteolysis during production of the nature identical EGF in a culture of a recombinant cell of the industrially useful organism. In a related method, following designing the modified amino acid sequence and prior to providing the modified EGF, the method further includes designing a nucleotide sequence encoding the modified amino acid sequence, the nucleotide sequence having codons selected for optimal usage in the industrially useful organism. In a related method, following designing the modified nucleotide sequence and prior to providing the modified EGF, the method further includes incorporating the modified nucleotide sequence into a vector, and transforming the vector into a cell of the industrially useful organism. In one embodiment, providing the modified EGF is providing a protein having an amino acid sequence as shown in SEQ ID NO: 2. The industrially useful organism is *Pichia pastoris*. In another embodiment, the invention provides a recombinant strain of *Pichia* obtained according to the method of a related embodiment.

In another embodiment, the invention provides a kit comprising at least one unit dosage of the composition of a composition herein in a pharmaceutically acceptable excipient. The kit according to a related embodiment further comprises an additional therapeutic agent. For example, the additional therapeutic agent is a growth receptor ligand; for example, the growth receptor ligand is a gastrin/cholecystokinin receptor ligand, for example, the ligand is gastrin. The unit dosage is sufficient for treatment of a subject in need of regeneration of a tissue. The tissue is a pancreatic islet or a gastric mucosa.

In another embodiment, the invention provides a transgenic animal carrying the nucleotide sequence encoding a composition herein having codons adjusted for optimum usage in an industrially acceptable organism, wherein the industrially acceptable organism is the animal. In a related embodiment, the nucleotide sequence contains additional regulatory sequence information for expression in a specific tissue. The animal can further contain an insertion mutation in the gene encoding nature identical endogenous EGF, such that production of the endogenous EGF of the animal is effectively knocked out.

BRIEF DESCRIPTION OF THE DRAWINGS

FIG. 1 panels A, B, C, and D show, respectively, amino acid sequences and nucleotide sequences encoding proteins and genes for EGF51N (SEQ ID NO: 2), EGF51A (SEQ ID NO: 3), EGF51Q (SEQ ID NO: 4), and EGF51S (SEQ ID NO: 5), which are modified forms of EGF, each having a chain length of 51 amino acids and a C-terminus residue which is asparagine, alanine, glutamine, or serine, respectively. The encoding genes are SEQ ID NOs: 6, 7, 8, and 9, respectively.

DESCRIPTION OF SPECIFIC EMBODIMENTS

Figure 2:
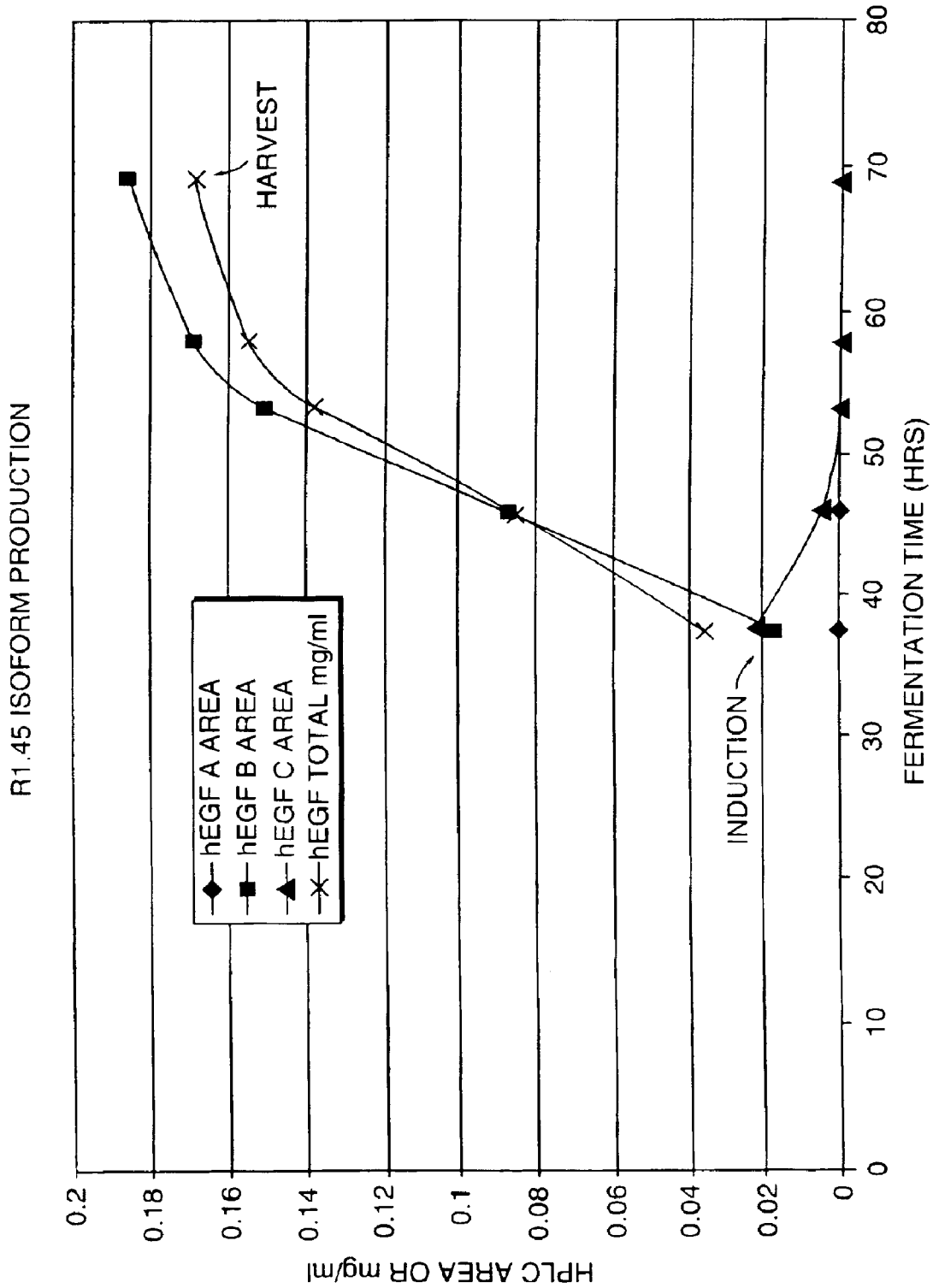
FIG. 2 shows production of EGF51N by *Pichia pastoris*. The amounts produced of each of three isoforms of amino acid residue lengths 49, 51, and 50, respectively, indicated as A, B, and C, and are shown as a function of time during the production, as is total amount of hEFG. Little to none of the A and C forms (49 or 50 amino acid residues in length) were observed, while EGF of 51 residues in length was continuously and stably produced as a function of growth of cells.

Human EGF was discovered in human urine and was named urogastrone due to its ability to inhibit acid secretion in the stomach (Gregory, H. et al. *Hoppe Seylers.Z.Physiol Chem.* 356, 1765–1774, 1975). In addition, EGF has mitogenic activity, i.e., it stimulates the growth of various cells and tissues (Karnes supra; Carpenter, G. et al. *J. Cell Physiol* 88, 227–237, 1976; Gasslander, T. et al. *Eur.Surg.Res.* 29, 142–149, 1997). EGF is also found to have a cytoprotective effect, stimulating migration of a cell toward a wound in vivo, or toward a gap introduced in a monolayer of cells in culture, to promote wound healing. These biological activities are specific to a family of structurally related growth factors, including EGF, TGF-α, amphiregulin and heparin binding EGF-like growth factor (Karnes, supra). The members of this family of growth factors have identical amino acids at 11 residues of the amino acid sequence, six of which are cysteine residues that form disulfide bonds.

Full length, natural (normal or wild-type) human epidermal growth factor (EGF) is a 53 amino acid protein with a molecular weight of 6217 daltons, the protein having a variety of biological functions in vivo and in vitro (Karnes, W., Epidermal growth factor and transforming growth factor alpha, 1994, Raven Press, New York). The term "natural EGF" as used herein shall mean full length, normal human EGF, as shown in SEQ ID NO: 1. The term "epidermal growth factor" or "EGF", as used throughout the specification and in the claims, refers to a polypeptide product or pharmaceutically acceptable salt thereof, which exhibits biological activities that are similar to natural human epidermal growth factor (hEGF; SEQ ID No: 1), as measured in one or more bioassays.

EGF receptor ligands include a family of proteins, including EGF and TGFα, capable of binding to a variety of EGF receptors on cells on various cell types in different tissues, and transmitting a signal to those cells, causing changes in growth and development of the particular cell type.

A number of forms of "modified EGF", varying from natural EGF in chain length and amino acid sequence, have been engineered and characterized as described herein. These modifications have been shown to affect both a biological activity and the rate of clearance of EGF. Further, the term includes peptides having the same or a similar amino acid sequence as hEGF, for example, with conservative amino acid substitutions at various residues. One or more of the last 5 amino acids from the C-terminus can be substituted with one or more other amino acids, or can be deleted.

Recombinant EGF having a methionine at position 21 replaced by a leucine residue has been described (U.S. Pat. No. 4,760,023). Recombinant hEGF was converted during storage from an aspartyl residue at position 11, to an isoaspartyl form that showed greatly reduced biological activity (George-Nascimento et al., *Biochemistry*, 29, 9584–9591, 1990). A series of nucleic acid molecules have been described that encode a family of protein that have significant similarity to EGF and TGF-α (WO 00/29438). EGF muteins (mutated EGF) having histidine at residue 16 replaced with a neutral or acidic amino acid have been described (WO 93/03757), such forms retaining activity at low values of pH. Chemical analogues and fragments of EGF and TGF-α retain ability to bind various members of the EGF receptor family (U.S. Pat. No. 4,686,283). Further, full length and other forms of EGF are susceptible in vivo and in vitro both to oxidation and proteolysis.

Embodiments of the present invention are based on the discovery that certain modifications to a C-terminus amino acid sequence of EGF, the C-terminus ranging from amino acid residue at position 48 to position 53, can result in forms of EGF that are resistant to endo- and exo-protease activity, and that retain full biological activities. These include EGF forms in which amino acids are deleted or replaced, for example, the basic amino acids at positions 48 (lysine in natural EGF) and 53 (arginine), the aromatic amino acids at positions 49 (tryptophan) and 50 (tryptophan), and the aliphatic amino acid at position 52 (leucine). The embodiments herein include pharmaceutically acceptable salts of the modified forms of EGF herein.

A "pharmaceutically acceptable carrier" includes any and all solvents, dispersion media, coatings, antimicrobials such as antibacterial and antifungal agents, isotonic and absorption delaying agents and the like that are physiologically compatible. Perferably, the carrier is suitable for intravenous, intramuscular, oral, intraperitoneal, transdermal, or subcutaneous administration. See, "Controlled Release of Drugs: Polymers and Aggregate Sytems", M. Rosoff, Ed., John Wiley, Inc., NY (1989).

As used herein, the term "pharmaceutically acceptable salt" refers to a salt that retains the desired biological activity of the parent compound and does not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like.

A physician or one having ordinary skill in the art can readily determine and prescribe an "effective dose" of the pharmaceutical composition required. For example, the physician could start administering a dose of the compound of the invention in the pharmaceutical composition at a level lower than that required in order to achieve the desired therapeutic effect, e.g., remediation of diabetes type I or type II or streptozoticin induced diabetes, and increase the dosage with time, until the desired effect is achieved, i.e., remediation of diabetes.

Dosage regimens can be adjusted to provide the optimum desired response, e.g., a therapeutic response, specifically herein remediation of a form of diabetes. A single dosage such as a single bolus can be administered, several divided doses can be administered over time, or the dose can be proportionally reduced or increased as indicated by the exigencies of the disease situation. A physician or other practitioner having ordinary skill in the pharmacological arts can readily determine and prescribe the effective dose of the required pharmaceutical composition. For example, the practitioner could start administering doses at a level lower than that required to achieve the desired therapeutic effect, and increase the dosage with time to obtain the desired effect, specifically, mitigation of symptoms of diabetes type I, type II, or streptozoticin induced diabetes. In general, a suitable effective dose of a modified EGF composition will be the lowest dose producing mitigation of symptoms such as mitigation of failure to respond to a glucose challenge by production of insulin and reduction in blood sugar concentration.

In another embodiment, a pharmaceutical composition herein includes also an additional therapeutic agent. Thus according to a method herein, a pharmaceutical composition which comprises a modified EGF can be administered as part of a combination therapey, in combination with an additional agent or agents, for example, in combination with a cholecystokinin receptor ligand.

A therapeutically effective dosage reduces symptomology by at least about 20%, at least about 40%, at least about 60%, or at least about 80%, compared to untreated subjects that have not received the composition.

The amino acids that occur in the various amino acid sequences referred to in the specification shall have their usual, three- and one-letter abbreviations, routinely used in the art. "Hydrophobic" amino acids include the aromatic amino acids, tyrosine, typtophan, and phenylalanine, and the aliphatic amino acids isoleucine, leucine, and valine. "Charged" amino acids include the acidic amino acids glutamic acid and aspartic acid, and the basic amino acids lysine and arginine. Other amino acids which are not charged are "neutral" amino acids.

A "conservative" amino acid substitution mutation shall mean that an amino acid found at a particular position in an EGF or a related molecule is replaced by one that is chemically similar. Examples of conservative amino acid substitution are: a charged amino acid replaced by a different amino of the same charge, such as Asp replaced by Glu, or an aromatic hydrophobic amino acid, e.g., Trp, replaced by a different aromatic hydrophobic amino acid, e.g., Phe (see U.S. Pat. No. 6,207,154, issued Mar. 27, 2001). A modified EGF, e.g., EGF51N, having in addition one or more conservative substitutions of amino acids, is considered to be encompassed within embodiments that are equivalent in the meaning of the various modified EGF composition, as described and claimed herein.

TABLE 1

Three letter and one letter amino acid abbreviations

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |

TABLE 1-continued

Three letter and one letter amino acid abbreviations

| Amino Acid | Abbreviation | |
|---|---|---|
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

One activity of EGF recently shown by Nardi et al. (U.S. Pat. Nos. 5,885,956, and 6,288,301) is that administration to a subject of an EGF receptor ligand in combination with a gastrin/cholecystokinin (CCK) receptor ligand enables a pancreatic islet precursor cell in the subject to differentiate, and to mature to an insulin-secreting cell. An EGF receptor ligand can thus play a role in causing differentiation of an undifferentiated progenitor cell, alone or in combination with another agent such as a CCK receptor ligand. A "progenitor" cell has the capability to divide for several generations, and to differentiate into a variety of different cell types.

EGF and other EGF receptor ligands have a mitogenic activity, and are capable of stimulating proliferation of cell number, particularly of an epithelial cell line in culture or in vivo. Yet another activity of an EGF receptor ligand is suppression of acid secretion, as demonstrated in an experimental animal, such as a fistulated animal, for example, a fistulated rat. EGF can further stimulate either or both of growth and differentiation of a tissue precursor cell.

The modified EGF compositions herein can be further modified to incorporate a chemical analog at one or more amino acid positions, for the purpose of inhibiting additional proteolysis that might shorten the pharmacological effectiveness of the modified EGF in vivo. While the modified EGF compositions as shown herein are demonstrably more resistant to proteolysis than is nature identical hEGF, it is anticipated that further chemical change which might be desirable is envisioned by the embodiments of the invention as described herein. Such further modifications include, for example, the presence of at least one D-amino acid substituted for a natural L-amino acid at a particular position, or the substitution of at least one alanine or another amino acid residue with a compound such as norvaline, acetyl-cysteine, or methylphenylglycine. An amino acid modification can also be N-methylation of a peptide backbone nitrogen.

The term "proteolysis" as used herein shall mean the process by which a protease or peptidase hydrolyzes a peptide bond, in the group of enzymes known as hydrolases. Proteolysis as used herein and in the claims includes both exopeptidase processive activities that sequentially release single amino acids from a terminus of the substrate protein, and endoprotease cleavage activities that produce two or more polypeptide, oligopeptide, or amino acid fragments following digestion of the substrate.

An "industrially useful organism" shall mean a strain of microorganism or cell line, generally regarded as safe, in which a therapeutic agent can be produced for administration to a human or animal, such that the organism does not contribute additional molecular entities that would provoke negative side effects or sequelae. A variety of bacteria have been used for industrial production, such as Streptomyces (see U.S. Pat. No. 4,745,056, issued May 17, 1988). For proteins that are sensitive to proteolytic degradation, species of fungi, for example, yeasts such as Saccharomyces species, for example, S. cerevisiae, and species of Pichia, for example, P. pastoris, are particularly useful for robust growth and production of a therapeutic protein, in the absence of significant contribution of other undesired molecular entities.

Further, the modified EGF forms as described herein, for example, EGF51N, can be manufactured in a transgenic animal, such as a mammal or a bird, under control of a regulatory element such that expression of the ectopic EGF can be directed to a convenient production medium, such as production in the milk of a transgenic animal which is a mammal, or production in the albumin of an egg of a transgenic animal which is a bird. Further, the endogenous gene of the transgenic animal can be inactivated by a knock out mutation, such that the human modified EGF is the sole EGF produced in the transgenic animal. See, U.S. Pat. No. 6,242,666, issued Jun. 5, 2001, and U.S. Pat. No. 6,271,436, issued Aug. 7, 2001).

The term "ectopic" as used here and in the claims refers to a gene isolated from a cell of one type of organism, e.g., a human cell, and which following genetic engineering technologies has been introduced into a cell of a different type of organism, such as a yeast, or a heterologous mammal such as a pig.

"Optimum codon usage" as used here and in the claims refers to adjusting the nucleotide sequence of a recombinant engineered gene to reflect differences in frequencies of the plurality of different trinucleotide codons encoding the same amino acid that are found in the genes within genomes of different organisms. All amino acids other than trp and met can be encoded by a plurality of codons. More particularly, the term optimum codon usage refers to a procedure whereby an engineered nucleotide sequence encoding a protein or polypeptide, and intended for insertion into a heterologous cell for production of the protein by in vivo methods in that cell, is altered in such a way from the naturally occurring gene that substantially the same natural amino acid sequence is encoded using different codons. The different set of codons as designed in the engineered gene is chosen according to the frequency of usage in the production cell, so that elements of the translational apparatus of the production cell will not limit the yield of product.

As used herein, the terms "protein", "peptide", and "polypeptide" shall have the same meaning.

The contents of all cited patents and publication are hereby incorporated by reference herein. The invention having been fully described is illustrated by Examples below, which shall not be construed as further limiting.

EXAMPLES

Example 1

Design and Synthesis of an EGF Gene Having Codons Optimized for Production, and Amino Acid Sequence Modifications for Enhanced Stability.

A foreign gene can be cloned and expressed in the industrially suitable yeast, Pichia pastoris, using a vector obtained, for example, from Invitrogen, Carlsbad, Calif. A kit containing cells, vectors, and media can be purchased. Protocols are available which can be downloaded, see www.invitrogen.com/context/tech-online/molecular_biology/manuals_pps. Optimization of codons in P. pastoris can be determined by methods described in U.S. Pat. No. 5,827,684, issued Oct. 27, 1998, and is available as a commercial service from Aptamer, Inc. (Rockville, Md.).

The amino acid sequence at the C-terminus of full length EGF is, from residues 48 to 53 KWWELR, using the one letter code defined above (see FIG. 1 panel A, and SEQ ID No: 1). Surprisingly, we found that a combination of deletion of at least one amino acid, and replacement of at least one amino acid, of the 5 C-terminus amino acids, resulted in a modified form of EGF that retains its biological activity and is resistant to proteolysis. Modifications of these amino acids include: deletion or replacements of the basic amino acids at positions 48 (which in natural EGF is lysine, K) and 53 (arginine, R), and of the aromatic amino acids at position 49 (tryptophan, W) and 50 (tryptophan, W), and the aliphatic amino acid at position 52 (leucine, L).

These amino acids are here identified as target substrates for various exo and endo proteases of the type that can be found in gastric fluid, in circulation, and in the culture media of production microorganisms such as *P. pastoris*. The peptide bonds between amino acids of the carboxy terminus of nature identical EGF are subject to digestion by several proteases and peptidases of known specificity. For example, the bond between residues 52 and 53, leu-arg, is subject to carboxypeptidase B activity; the bonds between each of 49–50 (trp—trp) and 50–51 (trp-glu) are subject to chymotrypsin; and the bond between 48–49 (lys-trp) is subject to trypsin digestion. (See "Proteolytic Enzymes", Ed. Beynon, R. and Bond J., IRL Press at Oxford, Appendix II, p. 232.) While additional proteases have other preferences or can be non-specific, neutral amino acids such as gln are not often a preferred substrate. An exception is the protease subtilisin, a product of the Gram positive soil bacterium *Bacillus subtilis*. For this reason, production of modified EGF having neutral or acid residues as described herein, in the bacterium *B. subtilis* is not preferred.

An embodiment of the invention is a composition which is a peptide comprising the amino acid sequence of human EGF having a length of 51 amino acids, in which the residue at position 51 is an amino acid other than glutamic acid, for example, asparagine (identified as EGF51N). A related embodiment is a nucleotide sequence encoding a gene for the modified EGF composition EGF51N (SEQ ID NO: 2), as shown in FIG. 1 panel B. This nucleotide sequence has been designed to be inserted into a vector such as an expression vector in an industrially acceptable production organism, for example, *Pichia pastoris*, for production of the composition, for use as a therapeutic agent. Similarly, EGF51A, EGF51Q, and EGF51S are further embodiments of the modified EGF forms. These modified forms are resistant to proteolysis as described herein (See FIG. 1 panels B, C, and D, respectively).

The design herein of a gene sequence encoding the modified EGF further uses codons that are optimal for recognition during protein synthesis in the production organism. These codons are substituted for the codons found in the natural human nucleotide sequence encoding EGF, in order to provide higher yields during growth of cells of the organism.

Further, data herein (infra) show that the design of the modified EGF in order to obtain resistance to proteolysis, for example, deleting two terminal amino acids at positions 52 and 53, and substituting asparagine for the naturally occurring glutamic acid at position 51, was successful in meeting this objective. Further, the modified form of EGF51N was found herein to have the desired biological activities, in particular, the ability to stimulate islet neogenesis to provide insulin in streptozotocin-induced diabetic rats, as shown in examples below.

Example 2

Yield of EGF from a Recombinant Organism Using a Synthetic Gene Having Codons Optimized for that Organism We found that the gene sequence shown in FIG. 1 used to produce EGF51N in *Pichia pastoris*, gave surprisingly high yields of the product in the fermentation production medium (see FIG. 2). The yield was comparable to that previously reported (U.S. Pat. No. 5,102,789 issued Apr. 7, 1992).

Example 3

Resistance of EGF51N to Proteolysis.

Further, determination of the molecular weight of the product and analysis of peptides obtained by digestion of the EGF51N confirmed that a single species of molecular weight that conformed to the predicted molecular weight, having a deletion of two amino acids compared to natural EGF, confirmed the identity of the material, and the production of a single species of EGF protein. During the time course of production of EGF51N, it was observed that the high yield of EGF obtained was characterized as a single molecular weight species (see FIG. 2). Thus, no significant proteolysis of the modified hEGF was observed in the fermentation medium.

Table 2 shows data obtained using another criterion indicating the resistance of EGF51N to protease activity, i.e., resistance in vitro to digestion with the enzyme carboxypeptidase B. These data show that between six and 30-fold more of EGF51N remains active following a course of incubation with carboxypeptidase B, compared to natural human EGF53. These data confirm that design of the C-terminus to eliminate residues that are substrates for enzyme digestion is effective in protecting the EGF during microbial production, and during exposure to other enzymes such as carboxypeptidase B in an environment such as in a subject.

TABLE 2

Resistance of EGF51N to carboxypeptidase B.

| Relative enzyme concentration | % EGF53 remaining | % EGF51N remaining |
|---|---|---|
| 0.01 | 75 | 75 |
| 0.1 | 1 | 30 |
| 1 (excess enzyme) | 1 | 6 |

The relative enzyme concentration is the ratio of carboxypeptidase to EGF.

Example 4

Biological Activity of EGF51N

Figure 3:
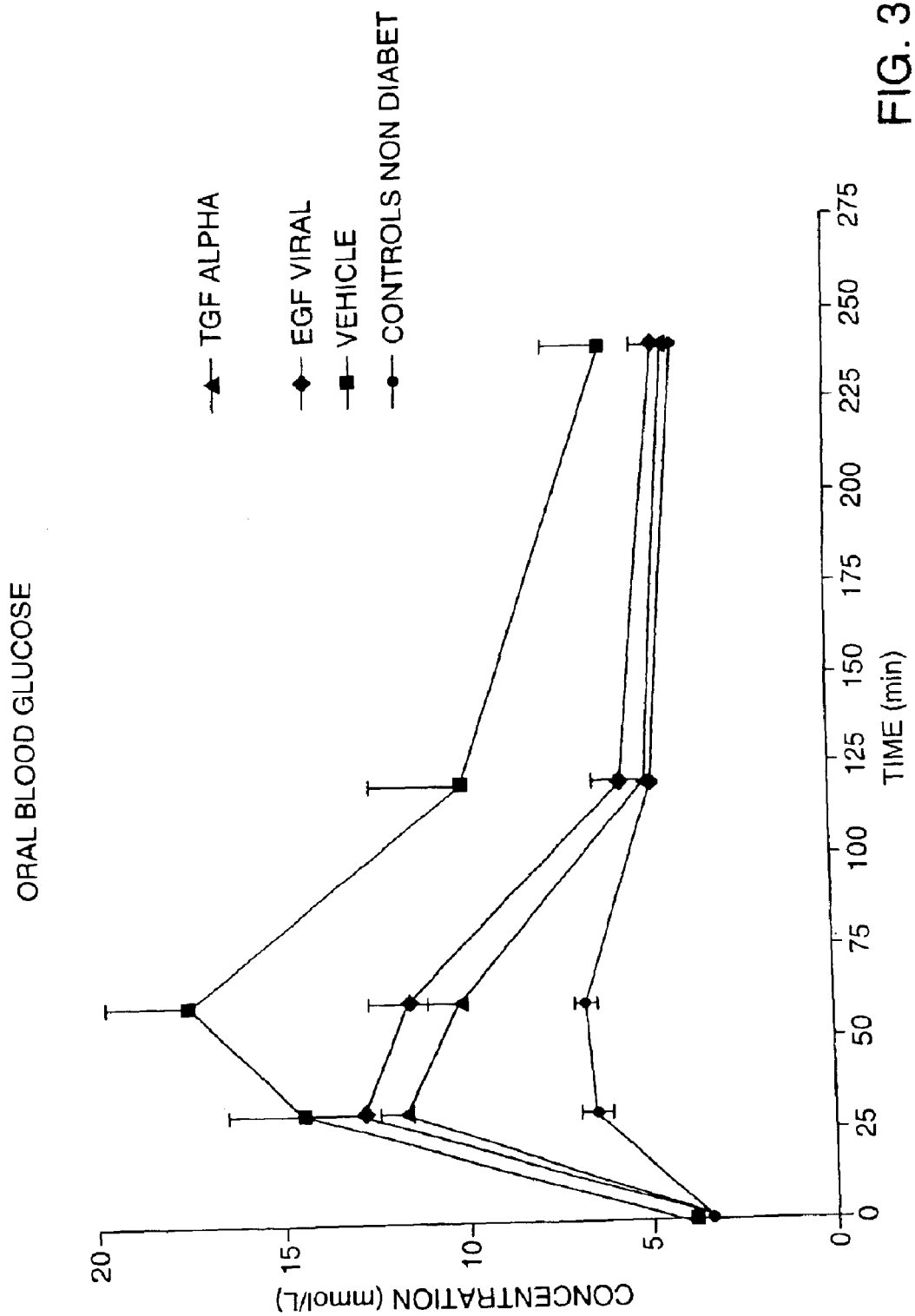
FIG. 3 shows results of treatment of streptozotocin-induced diabetic rats with 40 μg/kg/day of each of human gastrin and EGF51N, delivered intraperitoneally by continuous infusion for 14 days. After treatment, rats were evaluated for ability to restore plasma glucose to resting levels, shown on the ordinate, as a function of time in minutes shown on the abscissa, after an oral glucose challenge. Rapid restoration to resting levels of plasma glucose indicates biological activity of EGF51N.

EGF51N produced as above was used in an assay to measure to stimulation of islet neogenesis in vivo, as measured by lower blood concentration of treated animals to a subsequent challenge by glucose, to diabetic rats. Thus hEGF was found to have potency that is equivalent to the positive control TGFα, an alternative EGF receptor ligand (U.S. Pat. No. 6,288,301, issued Sep. 11, 2001) as shown in FIG. 3.

Further, the modified EGF51N was found to be capable of inhibiting gastric acid secretion in vivo in anaesthetized gastric fistula rats. After intravenous bolus injection of 8 µg EGF51N, the onset of inhibition of gastric acid production was found to have occurred within 10–20 minutes after injection, with a duration of inhibition of 20–50 minutes. This time of onset and duration of inhibition of acid secretion are comparable to that of the positive control, commercially obtained full length TGF-α.

These data indicate that the C-terminus modifications embodied in the EGF forms described herein, function both to protect EGF from proteolysis, and to maintain at least two different therapeutically important biological activities, inhibition of acid secretion and islet neogenesis therapy.

What is claimed is:

1. A modified EGF polypeptide composition comprising an amino acid sequence of length X, X being an integer that is at least 48 and not more than 53, such sequence (i) being at least 75% identical to that of positions 1–47 of SEQ ID NO: 1, and (ii) having at position X an amino acid residue different from that found in SEQ ID NO: 1, wherein the composition comprises a biological activity that is at least 50% of that of the polypeptide whose sequence is shown in SEQ ID NO: 1, the activity being selected from the group consisting of mitogenesis, cell growth stimulation, tissue growth stimulation, cytoprotection, inhibition of acid secretion, migration stimulation, wound healing, growth of a tissue precursor cell, differentiation of a tissue precursor cell, growth and differentiation of a tissue precursor cell, and EGF receptor binding.

2. A composition according to claim 1, wherein the amino acid residue at position X is a neutral amino acid.

3. A composition according to claim 1, wherein the amino acid residue at position X is asparagine.

4. A composition according to claim 3, wherein X is position 51.

5. A composition according to claim 1, having increased resistance to proteolysis in comparison with that of the polypeptide whose sequence is shown in SEQ ID NO: 1.

6. A composition according to claim 5, wherein the biological activity is at least 75% of that of the polypeptide whose sequence is shown in SEQ ID NO: 1.

7. A composition according to claim 6, wherein the biological activity is at least 90% of that of the polypeptide whose sequence is shown in SEQ ID NO: 1.

8. A composition according to claim 1, wherein mitogenesis is determined by rate of mitosis of epithelial cells.

9. A composition according to claim 1, wherein acid secretion is determined in a gastric fistulated animal.

10. A composition according to claim 1, wherein differentiation is determined by islet neogenesis or mucosal cell formation.

11. A composition according to claim 1, wherein the amino acid at position X is a hydrophobic amino acid.

12. A composition according to claim 1, wherein the amino acid at position X is a charged amino acid.

13. A composition according to claim 12, wherein the amino acid at position X is a negatively charged amino acid.

14. A composition according to claim 2, wherein X is selected from glutamine, alanine, and serine.

15. A composition comprising a modified EGF polypeptide having a length of 51 amino acids, wherein the modified EGF polypeptide has an amino acid sequence at least 75% identical to that of positions 1–47 of SEQ ID NO: 1, wherein the modified EGF polypeptide has a biological activity that is at least 50% that of the polypeptide of SEQ ID NO: 1, wherein the activity is selected from the group consisting of mitogenesis, cell growth stimulation, tissue growth stimulation, cytoprotection, inhibition of acid secretion migration stimulation, wound healing, growth of a tissue precursor cell, differentiation of a tissue precursor cell, growth and differentiation of a tissue precursor cell, and EGF receptor binding, and wherein the amino acid residue at position 51 of the modified EGF polypeptide is an amino acid other than glutamic acid.

16. A composition according to claim 15, wherein the biological activity of the composition is at least 75% of that of the polypeptide whose sequence is shown in SEQ ID NO: 1.

17. A composition according to claim 16, wherein the biological activity of the composition is at least 90% of that of the polypeptide whose sequence is shown in SEQ ID NO: 1.

18. A composition according to claim 15, the composition having a biological activity substantially equivalent to that of the polypeptide whose sequence is shown in SEQ ID NO: 1.

19. A composition according to claim 15, wherein the amino acid residues at positions 1–50 are at least 75% identical to that positions 1–50 of SEQ ID NO: 1.

20. A composition comprising a polypeptide having an amino acid sequence selected from the group consisting of SEQ ID NOs: 2, 3 and 4.

21. A composition comprising the polypeptide having the amino acid sequence of SEQ ID NO: 2.

22. A polypeptide of 51 amino acids in length, wherein the amino acid sequence of residues 1–50 are at least 75% identical to the amino acid sequence as shown in SEQ ID NO: 1, and residue 51 of the polypeptide is an asparagine residue, and wherein the polypeptide has a biological activity that is at least 50% that of the polypeptide having the amino acid sequence shown in SEQ ID NO: 1, the activity being selected from the group consisting of mitogenesis, cell growth stimulation, tissue growth stimulation, cytoprotection, inhibition of acid secretion, migration stimulation, wound healing, growth of a tissue precursor cell, differentiation of a tissue precursor cell, growth and differentiation of a tissue precursor cell, and EGF receptor binding.

23. A polypeptide according to claim 22, having increased resistance to proteolysis in comparison with that of the polypeptide having the amino acid sequence shown in SEQ ID NO: 1.

24. A polypeptide according to claim 22, wherein at least one of residues at positions 1–50 is a conservative substitution of an amino acid in the sequence as shown in SEQ ID NO: 1.

25. A polypeptide according to claim 22, further comprising a deletion of at least one of residues selected from amino acids at positions 1–5 as shown in SEQ ID NO: 1.

26. A composition comprising a human epidermal growth factor (EGF) polypeptide having an amino acid sequence at least 75% identical to that of at least positions 1–47 as shown in SEQ ID NO: 1, and having at least one amino acid replacement at positions 48–53 of SEQ ID NO:1 of the EGF carboxy terminus, wherein the polypeptide is more stable to proteolysis than a polypeptide having the amino acid sequence of a polypeptide having the amino acid sequence shown in SEQ ID NO: 1, the composition having a biological activity that is at least 50% that of SEQ ID NO: 1, the activity being selected from the group consisting of mitogenesis, cell growth stimulation, tissue growth stimulation, cytoprotection, inhibition of acid secretion, migration stimulation, wound healing, growth of a tissue precursor cell, differentiation of a tissue precursor cell, growth and differentiation of a tissue precursor cell, and EGF receptor binding.

27. A composition according to claim 26, comprising the amino acid sequence for residues at positions 1–50 substantially as shown in SEQ ID NO: 1, and in which the residue at position 51 is an amino acid other than glutamic acid.

28. A composition according to claim 27, in which the residue at position 51 is selected from the group consisting of asparagine, glutamine, alanine, and serine.

29. A composition according to claim 27, in which the residue at position 51 is asparagine.

30. A composition according to claim 26, wherein the biological activity is selected from the group consisting of mitogenesis, cytoprotection, inhibition of acid secretion, growth of a tissue precursor cell, differentiation of a precursor cell, and growth and differentiation of a precursor cell.

31. A composition according to claim 30, wherein mitogenesis is determined by rate of mitosis of epithelial cells.

32. A composition according to claim 30, wherein acid secretion is determined in a gastric fistulated animal.

33. A composition according to claim 30, wherein differentiation is determined by islet neogenesis or mucosal cell formation.

34. A composition comprising a therapeutically effective dose of the composition according to any of claims 1, 15 and 26 in a pharmaceutically acceptable excipient.

35. A composition according to claim 34, further comprising an additional therapeutic agent.

36. A composition according to claim 35, wherein the additional therapeutic agent is a growth factor receptor ligand.

37. A composition according to claim 36, wherein the ligand is a growth factor.

38. A composition according to claim 37, wherein the ligand is a gastrin/cholecystokinin receptor ligand.

39. A method of obtaining a composition comprising:
designing a gene encoding a polypeptide according to claim 1, wherein the gene comprises a nucleotide sequence having codons selected for optimum usage in an industrially acceptable organism; and
producing the composition in the organism by fermentation of the organism, wherein the organism includes the designed gene.

40. A kit comprising at least one unit dosage of the composition of any of claims 1, 15, and 26, in a pharmaceutically acceptable excipient.

41. A kit according to claim 40, further comprising an additional therapeutic agent.

42. A kit according to claim 41, wherein the additional therapeutic agent is a growth receptor ligand.

43. A kit according to claim 42, wherein the growth receptor ligand is a gastrin/cholecystokinin receptor ligand.

44. A kit according to claim 43, wherein the ligand is gastrin.

45. A kit according to claim 40, wherein the unit dosage is sufficient for treatment of a subject in need of regeneration of a tissue.

46. A kit according to claim 45, wherein the tissue is a pancreatic islet or a gastric mucosa.

47. A composition according to claim 1 comprising a polypeptide encoded by a nucleotide sequence having codons selected for optimum usage in an industrially acceptable organism.

48. A modified epidermal growth factor polypeptide comprising an amino acid sequence of length X, X being an integer that is at least 48 and not more than 53, such sequence (i) being at least 75% identical to that of positions 1–47 of SEQ ID NO. 1 and (ii) having at position X an amino acid residue different from that found in SEQ ID NO:1, wherein the polypeptide has the biological activity of a wild-type human epidermal growth factor, the activity being selected from the group consisting of mitogenesis, cell growth stimulation, tissue growth stimulation, cytoprotection, inhibition of acid secretion, migration stimulation, wound healing, growth of a tissue precursor cell, differentiation of a tissue precursor cell, growth and differentiation of a tissue precursor cell, and EGF receptor binding.

49. A modified epidermal growth factor polypeptide according to claim 48 having increased resistance to proteolysis compared with a polypeptide having the amino acid sequence of SEQ ID NO. 1, the activity being selected from the group consisting of mitogenesis, cell growth stimulation, tissue growth stimulation, cytoprotection, inhibition of acid secretion, migration stimulation, wound healing, growth of a tissue precursor cell, differentiation of a tissue precursor cell, growth and differentiation of a tissue precursor cell, and EGF receptor binding.

* * * * *